United States Patent [19]

Farthouat et al.

[11] 4,007,275
[45] Feb. 8, 1977

[54] N-(QUINOLYL)-ANTHRANILATES, THEIR COMPOSITIONS, AND USE

[75] Inventors: Anne Farthouat, Romainville; Jean Meier, La Varenne Saint-Hilaire, both of France

[73] Assignee: Roussel-UCLAF, Paris, France

[22] Filed: Dec. 10, 1975

[21] Appl. No.: 639,393

Related U.S. Application Data

[63] Continuation-in-part of Ser. No. 474,885, May 31, 1974, Pat. No. 3,944,555.

[30] Foreign Application Priority Data

June 13, 1973 France .............................. 73.21434

[52] U.S. Cl. ........................ 424/258; 260/287 AR; 260/283 S
[51] Int. Cl.[2] ...................................... C07D 215/44
[58] Field of Search .............. 260/287 AR; 424/258

[56] References Cited

UNITED STATES PATENTS 3,875,165  4/1975  Archibald et al. ........... 260/287 AR
3,910,898  10/1975  Allais et al. ................. 260/287 AR

*Primary Examiner*—Donald G. Daus
*Assistant Examiner*—David E. Wheeler
*Attorney, Agent, or Firm*—Hammond & Littell

[57] ABSTRACT

N-(7- or 8-substituted-quinolyl-4)-anthranilates of the formula

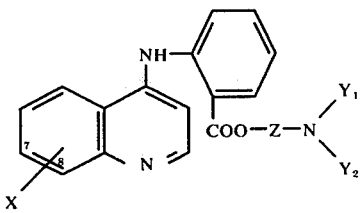

wherein X in the 7 or 8 position is trihalomethylthio, Z is $-(CH_2)_n-$ or $-(CH_2)_m-O-(CH_2)_p-$, $n$ is a whole number from 2 to 6, m and p are whole numbers from 2 to 3 and $Y_1$ and $Y_2$ are alkyl having 1 to 6 carbon atoms, as well as their non-toxic, pharmaceutically acceptable acid addition salts having analgesic and anti-inflammatory activity and their preparation.

6 Claims, No Drawings

N-(QUINOLYL)-ANTHRANILATES, THEIR COMPOSITIONS, AND USE

REFERENCE TO A PRIOR APPLICATION

This application is a continuation-in-part and division of our copending Patent Application Ser. No. 474,885, filed May 31, 1974, now U.S. Pat. No. 3,944,555.

OBJECTS OF THE INVENTION

It is an object of the invention to provide the novel anthranilates of the above formula I and their acid addition salts.

It is another object of the invention to provide a novel process for the preparation of the anthranilates of the above formula I.

It is a further object of the invention to provide novel analgesic and anti-inflammatory compositions.

It is an additional object of the invention to provide a novel method of treating pain and inflammation in warm-blooded animals.

These and other objects and advantages of the invention will become more apparent in the following description of the invention.

DESCRIPTION OF THE INVENTION

The novel compounds of the invention are selected from the group consisting of N-(7- and 8-substituted-quinolyl-4)-anthranilates of formula I:

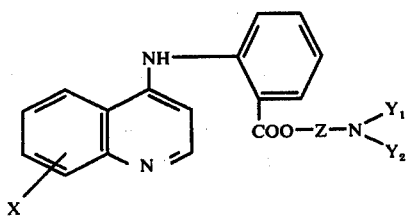

wherein X, in the 7 or 8 position, represents a trihalomethylthio group, Z represents the $-(CH_2)_n-$ group or the $-(CH_2)_m-O-(CH_2)_p-$ group, $n$ being a whole number between 2 and 6, $m$ and $p$ being whole numbers between 2 and 3, and $Y_1$ and $Y_2$ represent alkyl groups having 1 to 6 carbon atoms, as well as their non-toxic pharmaceutically acceptable acid addition salts.

In the formula I, the substituent X, which is preferably in the 8 position, particularly represents the trifluoromethylthio group, most preferably the 8-trifluoromethylthio; $n$ represents particularly the entire numbers 2, 3 or 4, preferably 2 or 3; and the substituents $Y_1$ and $Y_2$ preferably represent alkyl having from 1 to 4 carbon atoms, particularly methyl, ethyl, n-propyl, isopropyl, n-butyl or isobutyl.

More particularly the compounds of the invention are substituted anthranilates selected from the group consisting of N-(7- or 8-substituted-quinolyl-4)-anthranilates of the formula

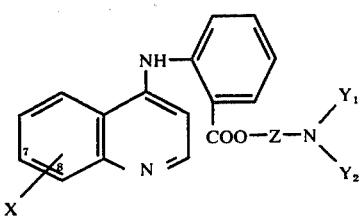

wherein X is trihalomethylthio in the 7 or 8 position, Z is a member selected from the group consisting of $-(CH_2)_n-$, where $n$ is an integer from 2 to 6, and $-CH_2)_m-O-(CH_2)_p-$, where $m$ and $p$ are each an integer from 2 to 3, and $Y_1$ and $Y_2$ are alkyl having from 1 to 6 carbon atoms, and their non-toxic, pharmaceutically acceptable acid addition salts.

Among the more interesting compounds of formula I as well as their acid addition salts are β-dimethylaminoethyl N-(8trifluoromethylthio-quinolyl-4)-anthanilate and its dihydrochloride, as are described hereafter in Example 1.

The novel compounds of formula I and their acid addition salts possess remarkable anti-inflammatory and analgesic activity. They are useful as therapeutics, for example, in the treatment of muscular, articular or nervous algias, of dental pains and migraine headaches, as well as of inflammatory reactions, particularly of rheumatic disturbances, of lumbagos, of zonas, and also in the complementary treatment of infectious or febrile states. Thus the compounds of formula I, as well as their pharmaceutically acceptable acid addition salts, can be employed as medicaments.

Examples of suitable acids for the non-toxic pharmaceutically acceptable acid addition salts are mineral acids such as hydrochloric acid, hydrobromic acid, sulfuric acid, phosphoric acid, etc. and organic carboxylic acids such as acetic acid, benzoic acid, tartaric acid, citric acid, maleic acid, malonic acid, fumaric acid, etc., or organic sulfonic acids, such as methanesulfonic acid or p-toluenesulfonic acid, etc.

The anti-inflammatory and analgesic compositions of the invention are comprised of at least one compound of formula I or its non-toxic, pharmaceutically acceptable acid addition salt, preferably β-dimethylaminoethyl N-(8-trifluoromethyl-quinolyl-4)-anthranilate dihydrochloride, and a major amount of a pharmaceutical carrier. These pharmaceutical compositions may be administered parenterally, orally or rectally, or locally in a topical application on the skin or mucous membranes.

To this effect, the pharmaceutical compositions may be in the form of injectable solutions or suspensions, of tablets, of coated tablets, of sachets, of capsules, of gelules, of drinkable solutes or emulsions, of suppositories, of pomades, or of topical creams or powders. These pharmaceutical forms are prepared according to the usual methods.

The novel method of treating pain and inflammations in warm-blooded animals comprises administering to warm-blooded animals a safe and effective amount of at least one compound of formula I or its non-toxic, pharmaceutically acceptable acid addition salts. The said compounds may be administered orally, perlingually, transcutaneously, rectally or topically on skin or mucous membranes. The usual useful daily dose is 0.9 to 5 mg/kg depending upon the method of administration. The total daily dose in the adult, for example, can be varied between 100 and 500 mg of active principle, when administered orally.

The active principle or principles can be mixed with various pharmaceutical excipients usually employed in pharmaceutical compositions, such as talc, gum arabic, lactose, starch, magnesium stearate, cocoa butter, aqueous or non-aqueous vehicles, fats of animal or vegetable origin, paraffinic derivatives, glycols, various emollients, dispersants or emulsifiers and preservatives.

The compounds of formula I can be prepared according to the usual processes for the preparation of esters. In particular, the compounds of formula I are prepared by a transesterification process which is characterized in that a compound of the formula II:

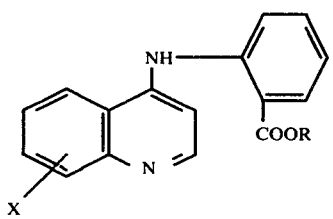

wherein X has the above-assigned values, and R is a lower alkyl, preferably containing from 1 to 6 carbon atoms, is reacted with an alcohol of the formula III:

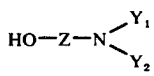

wherein Z, $Y_1$ and $Y_2$ have the above-assigned values. The acid addition salts of the compounds of formula I are prepared according to the usual methods. Preferably R is methyl, ethyl, propyl or butyl.

This transesterification reaction is advantageously effected in the presence of an alkaline media, such as an alkali metal hydride, an alkali metal amide or an alkali metal lower alkanolate.

The starting compounds of formulas II and III are either described in the literature, or accessible by means of general methods described in the literature. Compounds of formula II can be prepared by the processes described in French Patent Application No. 73 08677.

In the following examples there are described several preferred embodiments to illustrate the invention. However, it should be understood that the invention is not intended to be limited to the specific embodiments.

EXAMPLE 1

β-dimethylaminoethyl
N-(8-trifluoromethylthio-quinolyl-4)-anthranilate
dihydrochloride Step A:

β-dimethylaminoethyl
N-(8-trifluoromethylthio-quinolyl-4)-anthranilate 11 gm of methyl N-(8-trifluoromethylthio-quinolyl-4)-anthranilate (prepared as indicated in French Patent Application 73 08677) were introduced into a solution containing 90 cc of toluene and 90 cc of dimethylaminoethanol. The solution was distilled to a volume of about 100 cc. The solution thus obtained was cooled to about 50°C and 160 mg of sodium hydride in a 50% suspension in mineral oil was added thereto. The mixture was then heated for two and a half hours under a slight vacuum while distilling off the methanol formed.

The mixture was then allowed to return to room temperature and extracted with ether. The ethereal extracts were washed with water and dried over sodium sulfate. The solvent was evaporated to dryness under vacuum. 5 gm of β-dimethylaminoethyl N-(8-trifluoromethylthio-quinolyl-4)-anthanilate were obtained in the form of a yellow oil.

Step B:

β-dimethylaminoethyl
N-(8-trifluoromethylthio-quinolyl-4)-anthranilate
dihydrochloride 5 gm of the product prepared in Step A was introduced into 3 cc of methanol. 5 cc of a 5N hydrochloric acid solution in ethanol was added thereto. The product was caused to precipitate by the addition of 100 cc of ether. The mixture was maintained under agitation for a period of 12 hours and then filtered and dried. 5.2 gm of β-dimethylaminoethyl N-(8-trifluoromethylthio-quinolyl-4)-anthranilate dihydrochloride were obtained melting at 175° C.

EXAMPLE 2

Preparation of Tablets

Tablets were prepared corresponding to the following formula:

| | |
|---|---|
| Compound of Example 1 | 50 mg |
| Excipient sufficient for 1 tablet containing | 350 mg |

The excipient consisted of starch, lactose, talc and magnesium stearate.

Any of the compounds included in the generic formula I can be substituted in the above formulation with the same results.

PHARMACOLOGICAL DATA

Analgesic Effect: Acetic Acid Test

The test employed was based on the fact noted by Koster et al (Fed. proc. 1959, 18, 412) according to which the intraperitoneal injection of acetic acid provoked repeated characteristic movements of stretching and twisting which persisted in mice for more than 6 hours. Analgesics prevent or suppress this syndrome which is an exterior manifestation of a diffuse abdominal pain.

A solution of 1% of acetic acid in water containing 10% of gum arabic was employed. The dose provoking the syndrome in mice under these conditions was 0.01 cc/gm, being 100 mg/kg of acetic acid.

The product studied was administered orally to groups of five mice, which had not been fed for 24 hours, a half hour before the intraperitoneal injection of the acetic acid. The stretchings were observed, noted and counted for each mouse, during a period of observation of 15 minutes immediately after the injection of acetic acid.

The results are expressed on the basis of the $DA_{50}$, that is, the dose which permits obtaining a 50% diminution of the number of stretchings with reference to the control animals.

The results of the test for the compound, β-dimethylaminoethyl N-(8-trifluoromethylthio-quinolyl-4)-anthranilate dihydrochloride, gave a DA₅₀ of 30 mg/kg.

The preceding specific embodiments are illustrative of the practice of the invention. It is to be understood, however, that other expedients known to those skilled in the art or disclosed herein may be employed without departing from the spirit of the invention or the scope of the appended claims. We claim:

1. Substituted anthranilates selected from the group consisting of N-(7- or 8-substituted-quinolyl-4)-anthranilates of the formula

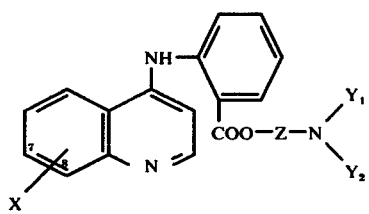

wherein x is trihalomethylthio in the 7 or 8 position, Z is a member selected from the group consisting of —(CH₂)ₙ—, where $n$ is an integer from 2 to 6, and —(CH₂)ₘ—O—(CH₂)ₚ—, where $m$ and $p$ are each an integer from 2 to 3, and Y₁ and Y₂ are alkyl having from 1 to 6 carbon atoms, and their non-toxic, pharmaceutically acceptable acid addition salts.

2. The substituted anthranilates of claim 1 wherein Y₁ and Y₂ are alkyl having from 1 to 4 carbon atoms.

3. The substituted anthranilates of claim 1 wherein X is 8-trifluoromethyl, Y₁ and Y₂ are alkyl having from 1 to 4 carbon atoms, X is —(CH₂)ₙ—, and $n$ is an integer from 2 to 4.

4. Substituted anthranilates of claim 3 selected from the group consisting of β-dimethylaminoethyl N-(8-trifluoromethylthio-quinolyl-4)-anthranilate and its dihydrochloride.

5. An analgesic and anti-inflammatory composition comprising an analgesically and anti-inflammatorily effective amount of a compound of claim 1 and a major amount of a pharmaceutical carrier.

6. A method of relieving pain and inflammation in warm-blooded animals which comprises administering to warm-blooded animals a safe and effective amount for relieving pain and inflammation of a compound of claim 1.

* * * * *